US00PP35325P2

(12) United States Plant Patent
Olesen

(10) Patent No.: US PP35,325 P2
(45) Date of Patent: Aug. 22, 2023

(54) ROSE PLANT NAMED 'POULREN035'

(50) Latin Name: *Rosa hybrida*
Varietal Denomination: Poulren035

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,611

(22) Filed: Sep. 13, 2022

(30) Foreign Application Priority Data

Sep. 24, 2021 (QZ) ..... PBR 2021/2358

(51) Int. Cl.
*A01H 5/02* (2018.01)
*A01H 6/74* (2018.01)

(52) U.S. Cl.
USPC ..... Plt./137
CPC ..... *A01H 6/749* (2018.05)

(58) Field of Classification Search
USPC ..... Plt./137
CPC ..... A01H 6/749; A01H 5/02
See application file for complete search history.

*Primary Examiner* — Keith O. Robinson

(57) ABSTRACT

A new garden rose plant of the Hybrid Tea class which has abundant, light pink flowers and attractive foliage. This new and distinct variety has shown to be uniform and stable in the resulting generations from asexual propagation.

2 Drawing Sheets

Botanical designation: *Rosa hybrida.*

Variety denomination: 'Poulren035'.

This application claims priority to Plant Breeder's Rights Application Number 2021/2358, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulren035', originated as a single seedling from the stated cross.

The new variety may be distinguished from its male pollen parent and female seed parent primarily by the following characteristics. While the male pollen parent plant has light pink flowers 60 mm in diameter with 40 petals, the new variety has light pink flowers 85 mm in diameter with 105 petals. The female seed parent plant has red flowers while the new variety has light pink flowers.

The objective of the hybridization of this rose variety was to create a new and distinct variety with unique qualities, such as:

1. Uniform and abundant light pink flowers;
2. Vigorous, but compact growth when propagated on its own roots;
3. Exceptional disease resistance; and
4. Perfumed flowers.

This combination of qualities is not present in previously available commercial cultivars of this type, known to the inventor, and distinguish 'Poulren035' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulren035' was selected in the spring of 2015 by the inventor as a single plant from the progeny of the aforementioned hybridization.

Asexual reproduction of 'Poulren035' by rooted cuttings was first done by Mogens N. Olesen in the nursery in Fredensborg, Denmark in July, 2015. This initial and other subsequent asexual propagations conducted in controlled environments have demonstrated that the characteristics of 'Poulren035' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren035'.

Specifically illustrated in FIG. 1 of the drawings are open flowers viewed from above and the side, flower petals detached revealing reproductive flower parts, sepals detached revealing the receptacle and pedicel.

Figure 1:
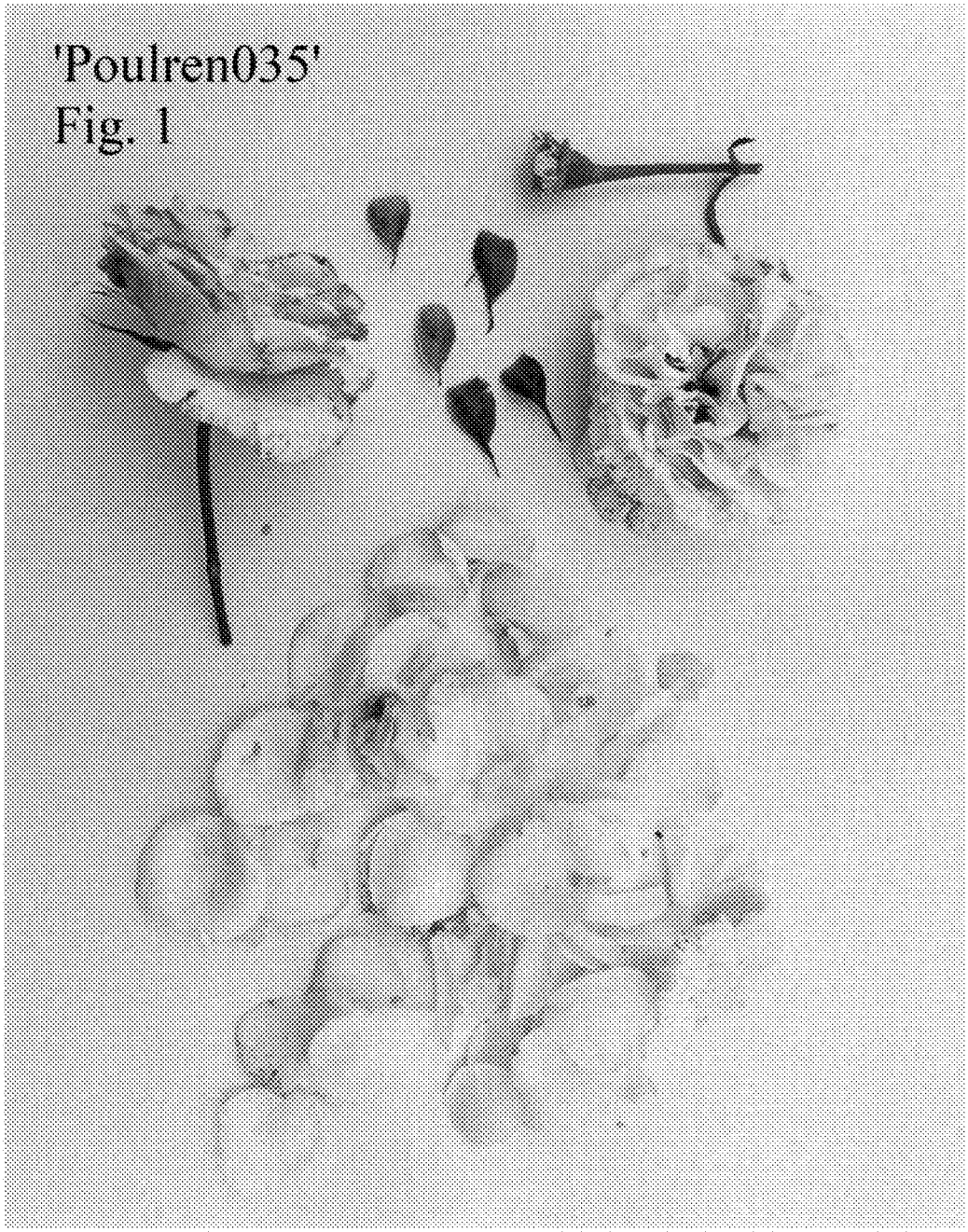
Figure 2:
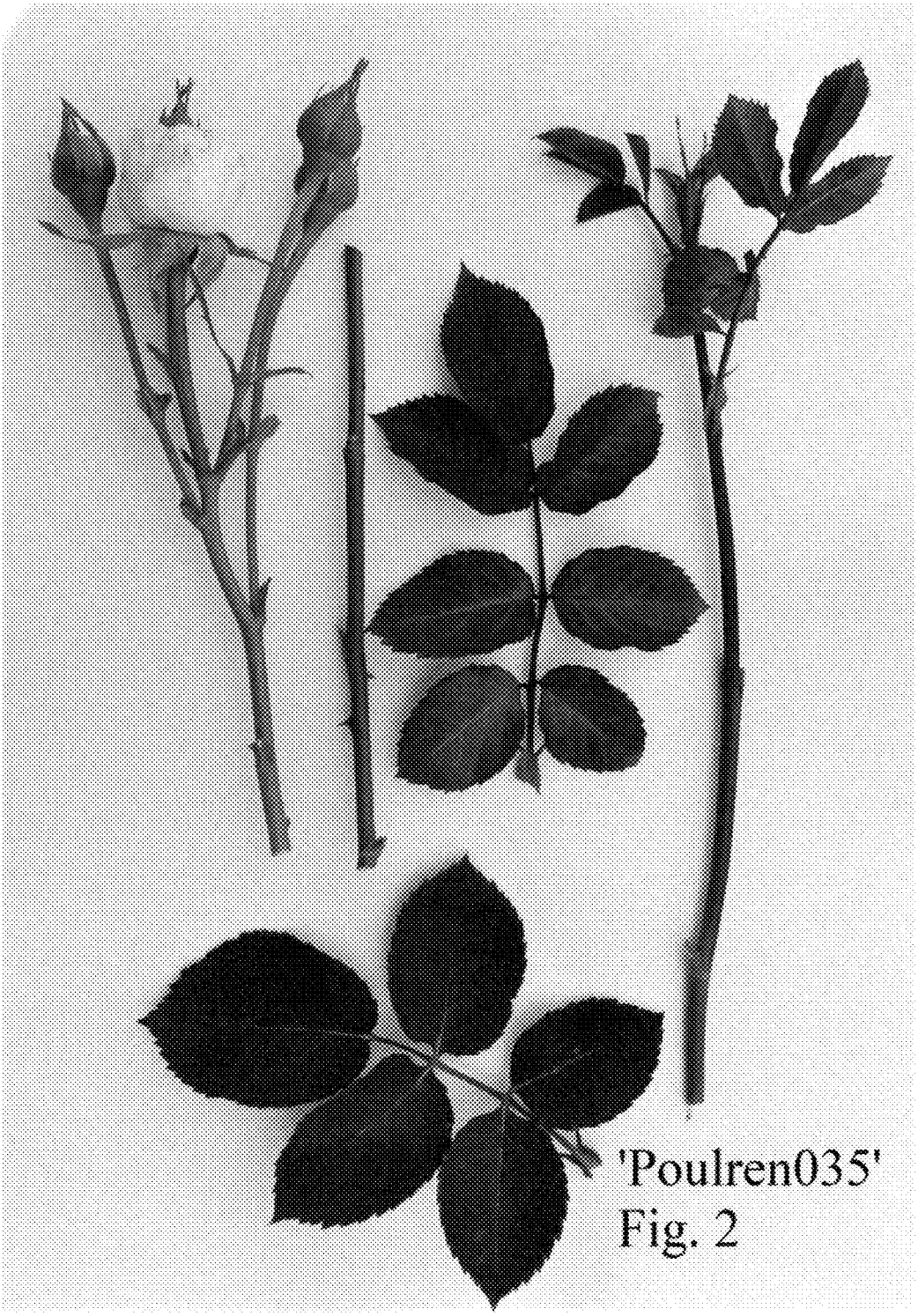

Specifically illustrated in FIG. 2 of the drawings are mature and juvenile compound leaves, juvenile and mature bare stems, and a cluster of flower buds on a branch. Plants shown are 2 years of age.

DETAILED DESCRIPTION OF THE VARIETY

The following is a description of 'Poulren035', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulren023', U.S. Plant Pat. No. 27,656 are now compared to 'Poulren035'. While the comparison variety has 25 to 30 flower petals with a flower diameter of 105 mm, the newly claimed plant has 105 flower petals and a flower diameter of 85 mm. In terms of general tonality of flower colour, the claimed plant is Red Group 56B, and the comparison variety is Red Group 49A and Red-Purple Group 62D.

FLOWER AND FLOWER BUD

Blooming habit: Continuous.

Flower bud:

- *Size.*—Upon opening, 26 mm in length from base of receptacle to end of bud. Bud diameter is 18 mm.
- *Bud form.*—Ovoid.
- *Bud color.*—As sepals divide petals are Yellow-White Group 158A.
- *Sepal inner surface.*—Color: Yellow-Green Group 146D. Surface: Lightly pubescent.
- *Sepal outer surface.*—Color: Yellow-Green Group 144A with intonations of Greyed-Red Group 181A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—About 31 mm long, 12 mm wide.
- *Receptacle.*—Texture: Smooth. Size: 10 mm in height, 11 mm wide. Color: Yellow-Green Group 144A. Shape: Campanulate.
- *Pedicel.*—Surface: Rough with small prickles and stipitate glands. Length: 60 mm on average. Diameter: 3.5 mm on average. Color: Yellow-Green Group 146D. Strength: Strong.
- *Peduncle.*—Length: About 4 cm. Diameter: About 3 mm. Color: Yellow-Green Group 145A. Texture: Smooth.

Flower bud development: Flower buds are borne in clusters of 3 to 5 flower buds per stem. Development as a panicle.

Flower bloom:

- *Fragrance.*—Strong rose perfume.
- *Duration.*—The blooms have a duration on the plant of approximately 14 days. Petals fall cleanly away from plant after flowers have fully matured.
- *Size.*—Flower diameter is 85 mm when open. Flower depth is 38 mm.
- *Flower shape.*—Open cup, very double flower, with petals that curve out from the center.
- *Shape of flower, side view.*—The upper portion is flat convex. The lower portion is concave.

Petalage: Under normal conditions, flowers have about 105 petals.

General tonality of flower: Open flowers are Red Group 56B.

Petal color:

- *Upon opening, outer petals.*—Upper surface: White Group 155A. Lower surface: White Group 155A.
- *Upon opening, inner petals.*—Upper surface: Red Group 38B. Yellow Group 8B at the basal point of attachment. Lower surface: Orange Group 29C. Yellow Group 8B at the basal point of attachment.
- *Basal petal spots, upon opening.*—Upper surface: Yellow-Green Group 145D. Lower surface: Yellow-Green Group 145D.
- *After opening, outer petals.*—Upper surface: White Group 155A. Lower surface: White Group 155A.
- *After opening, inner petals.*—Upper surface: White Group 155A with intonations of Red Group 49B. Lower surface: White Group 155A with intonations of Red Group 49B.
- *Basal petal spots, after opening.*—Upper surface: Yellow-Green Group 145D. Lower surface: Yellow-Green Group 145D.

Petals:

- *Petal reflex.*—Somewhat reflexed.
- *Margin.*—Clefts, moderate undulations.
- *Shape.*—Broad and elliptic. Apex shape: Rounded. Base shape: Acute.
- *Size.*—40 mm (l)×45 mm (w).
- *Texture.*—Smooth.
- *Thickness.*—Average.

Petaloids:

- *Size.*—11 mm (l) by 9 mm (w).
- *Quantity.*—About 20.
- *Shape.*—Rounded to elliptical with an acute base and rounded apex.
- *Color.*—White Group 155A with intonations of Red Group 49B. At the basal zone Yellow-Green Group 145D.

Reproductive flower parts:

- *Pollen.*—None observed.
- *Anthers.*—Size: 3 mm in length. Color: Yellow-Orange Group 22A. Quantity: 42 on average.
- *Filaments.*—Color: Yellow Group 7B. Length: 4 mm.
- *Pistils.*—Length: 4 mm. Quantity: 28 on average.
- *Stigmas.*—Color: Greyed-Yellow Group 160D.
- *Styles.*—Color: Green-White Group 157A with intonations of Red-Purple Group 58B.
- *Location of stigmas.*—Level in location relative to the length of the filaments and the height of the anthers.
- *Hips.*—None Observed.

PLANT

- *Plant growth.*—Upright. Plants are 55 cm in height, and 50 cm wide.

Stems:

- *Color of juvenile growth.*—Yellow-Green Group 146B with intonations of Greyed-Purple Group 183B.
- *Color of mature growth.*—Yellow-Green Group 144A.
- *Length.*—Canes are about 18 cm from the base of the plant to the flowering portion.
- *Diameter.*—About 5 mm.
- *Internodes.*—About 55 mm between nodes.
- *Surface texture.*—Young wood: Smooth. Older wood: Smooth.

Long prickles:

- *Incidence.*—About 4 prickles per 10 cm of stem.
- *Size.*—Average length of prickles on mature stems is 6 mm.
- *Shape.*—Upper portion is linear. Lower portion is concave.

*Color*.—Juvenile prickles: Greyed-Red Group 180C. Mature prickles: Greyed-Red Group 180C.

Plant foliage:

*Compound leaf*.—150 mm (1)×120 (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 19 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 36 mm. Diameter: 2 mm. Upper surface color: Yellow-Green Group 146A. Lower surface color: Yellow-Green Group 144A.

*Rachis*.—Length: 41 mm. Upper surface color: Yellow-Green Group 146A. Lower surface color: Yellow-Green Group 144A.

*Leaflet*.—Quantity: Normally 5, occasionally 7 leaflets. Margins: Serrated. Size: Terminal leaflets are about 66 mm long, 54 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren035' substantially as described and illustrated herein.

* * * * *

'Poulren035'

'Poulren035'